United States Patent [19]

Hayashi et al.

[11] Patent Number: 4,980,474
[45] Date of Patent: Dec. 25, 1990

[54] APOVINCAMINIC ACID DERIVATIVES

[75] Inventors: Masatoshi Hayashi, Saitama; Sadakazu Yokomori, Urawa; Yoshimoto Nakashima, Ageo; Katsuo Hatayama, Omiya, all of Japan

[73] Assignee: Taisho Pharmaceutical Co., Ltd., Japan

[21] Appl. No.: 405,972

[22] Filed: Sep. 12, 1989

[30] Foreign Application Priority Data

Sep. 30, 1988 [JP] Japan .................. 63-246884

[51] Int. Cl.$^5$ .................. C07D 461/00; A61K 31/435
[52] U.S. Cl. ........................................................ 546/51
[58] Field of Search ...................... 546/43, 51; 514/283

[56] References Cited

U.S. PATENT DOCUMENTS 3,966,745 6/1976 Guidicelli et al. .................. 546/51
4,540,701 10/1985 Ueda et al. ........................ 546/338
4,613,608 9/1986 Ueda et al. ........................ 546/338
4,839,362 6/1989 Kreidl et al. ....................... 546/51

OTHER PUBLICATIONS

Ban et al., "Apovincaminic Acid Esters", CA 105: 43143c (1986).

*Primary Examiner*—Mark L. Berch
*Assistant Examiner*—Celia Chang
*Attorney, Agent, or Firm*—Lorusso & Loud

[57] ABSTRACT

An apovincaminic acid derivative represented by the formula

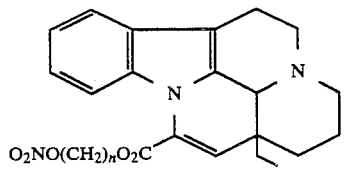

wherein n is an integer of from 2 to 11, and a pharmaceutically acceptable salt thereof are disclosed. These compounds are useful for therapy of cerebrovascular injuries, peripheral vessel injuries, angina pectoris, hypertension and senile dementia.

3 Claims, No Drawings

# APOVINCAMINIC ACID DERIVATIVES

BACKGROUND OF THE INVENTION

1. Field of the Invention

The present invention relates to apovincaminic acid derivatives, and more particularly relates to apovincaminic acid derivatives having high therapeutic effect on cerebrovascular injuries, peripheral vessel injuries, angina pectoris and hypertension.

2. Description of the Prior Art

In the past, there have been known apovincaminic acid derivatives having high therapeutic effect on cerebrovascular injuries, peripheral vessel injuries, angina pectoris and hypertension in Japanese Patent Kokai Nos. 56-71091 and 59-62590. However, the pharmacological activity of these compounds is not sufficient, and there is a need for appearance of apovincaminic acid derivatives having stronger pharmaceutical effect on cerebrovascular injuries, peripheral vessel injuries, angina pectoris and hypertension.

As a result of various researches, the present inventors have found that certain nitroxyalkyl esters of apovincaminic acid have an excellent increase effect on blood flow and an antihypertensive effect, and have accomplished the present invention.

SUMMARY OF THE INVENTION

An object of the present invention is to provide an apovincaminic acid derivative represented by the formula $O_2NO(CH_2)_nO_2C$ (wherein n is an integer of from 2 to 11), and a pharmaceutically acceptable salt thereof.

DETAILED DESCRIPTION OF THE INVENTION

The pharmaceutically acceptable salts of the compound of Formula I are those derived by adding inorganic or organic acids to the compound of Formula I. The inorganic and organic acids, but not limited thereof, are hydrochloric acid, hydrobromic acid, sulfuric acid, phosphoric acid, formic acid, acetic acid, propionic acid, glycolic acid, fumaric acid, succinic acid, tartaric acid, ascorbic acid, sulicylic acid, lactic acid, malic acid, methanesulfonic acid and p-toluenesulfonic acid.

Racemic form and optically active forms of the apovincaminic acid derivatives are all included within the scope of the present invention, but (+)-apovincaminic acid derivatives are especially preferred.

Among the preferred compounds of the present invention are the compounds of Formula I wherein n is 2 or 3, e.g., 2-nitroxyethyl apovincaminate and 3-nitroxy-n-propyl apovincaminate.

The compounds of the present invention can be prepared, for example, by the following process:

Apovincaminic acid is first reacted with an ordinary reagent being capable of converting a carbonic acid to an acid chloride in an inert solvent at a temperature of the boiling point of the solvent to give apovincaminic acid chloride.

The ordinary reagents being capable of converting a carbonic acid to an acid chloride may be thionyl chloride, phosphorus oxychloride, phosphorus pentachloride and the like. The inert solvents may be dichloroethane, chloroform, carbon tetrachloride, benzene, toluene, xylene and N,N-dimethylformamide, and these solvents can be used alone or in combination with the other solvents. The reaction time is from 10 minutes to 3 hours.

Then, apovincaminic acid chloride is reacted with a compound of the formula $$HO(CH_2)_nONO_2 \qquad II$$

(wherein n is as defined above), in an inert solvent in the presence of a base to give a compound of Formula I.

Examples of the base are triethylamine, pyridine, collidine and diisopropylethylamine. Examples of the inert solvent used are the same as those exemplified in the acid chlorination of apovincaminic acid. The reaction time is from 1 to 12 hours, and the reaction temperature is from 0° C. to the boiling point of the solvent.

The compound of Formula II can be prepared by recting a compound of the formula $HO(OH_2)_nBr$ (wherein n is as defined above) with silver nitrate, or by reduction of a compound of the formula $O_2NO(CH_2)_n-CO_2R$ (wherein n is as defined above, and R is a hydrogen atom or a residual group of any alcohol). For the reduction, there can be used reducing agents such as alminium lithium hydride, sodium borohydride, potassium borohydride and the like.

The compounds of the present invention can be also prepared by reacting apovincaminic acid with a nitroxyalkyl halide represented by the formula $$Y(CH_2)_nONO_2$$

(wherein Y is a halogen atom and n is as defined above) in an organic solvent in the presence of a base. Examples of the base used herein are potassium carbonate, triethylamine, pyridine, sodium hydrogen carbonate, sodium hydroxide and potassium hydroxide. Examples of the organic solvent are dimethyl sulfoxide, N,N-dimethylformamide, acetone, acetonitrile and tetrahydrofuran.

The compounds of the present invention show excellent cerebral vasodilation, inhibition of vessel contraction and improvement of abnormalities of electroencephalogram (EEG), and therefore they are useful for thereby of cerebrovascular injuries, peripheral vessel injuries, angina pectoris, hypertension and senile dementia. For these purposes, these compounds can be administered orally or parenterally in a conventional dosage forms such as tablets, powders, granules, capsules, solutions, emulsions, suspensions, injectional solutions and the like, each of which can be prepared in accordance with ordinary pharmaceutical practices.

The dosage of the compound of the present invention depends on the age, body weight and response of the patient, route of administration or time of administration, but usually it may be from 1 to 100 mg per day.

The present invention is illustrated by the following examples in more detail.

EXAMPLE 1

Preparation of 3-nitroxy-n-propyl apovincaminate

In 200 ml of benzene were suspended 6.44 g (20 mmole) of apovincaminic acid 3.6 ml (50 mmole) of thionyl chloride and 2 ml of N,N-dimethylformamide, and then the suspension was heated at reflux for 30 minutes. The reaction solution was concentrated under reduced pressure, 50 ml of benzene was added to the residue, and the mixture was stirred for 10 minutes. To the resulting suspension was added dropwise a mixture of 3 g (30 mmole) of 3-nitroxy-n-propanol, 20 ml of triethylamine and 20 ml of benzene. After stirring for 4 hours, the reaction solution was poured into water, and extracted with ether (300 ml×2). The ethereal layer was successively with water and a saturated aqueous sodium chloride solution, dried over anhydrous sodium sulfate, and concentrated under reduced pressure to give 6.5 g of the crude product.

The crude product was purified by silica gel column chromatography [Wako-gel C-200 (trade name of Wako Junyaku Industries Co.), eluent: ether]. The eluted solution was concentrated, and the residue was recrystallized from ether - hexane to give 4.8 g of the title compound as colorless prisms.

m.p. 88°–90° C.
$^1$H-NMR (CDCl$_3$, 200 MHz)δ ppm
7.0–7.6 (4H, m), 6.16 (1H, s),
4.4–4.7 (4H, m), 4.16 (1H, s),
2.8–3.5 (3H, m), 2.4–2.7 (3H, m),
2.20 (2H, quintet, J=7 Hz), 1.2–2.1 (5H, m),
1.01 (3H, t, J=7 Hz), 0.98 (1H, m).

EXAMPLE 2

Preparations of 6-nitroxy-n-hexyl apovincaminate hydrochloride

In 70 ml of benzene were suspended 2 g (6.2 mmole) of apovincaminic acid, 1.1 ml (15 mmole) of thionyl chloride and 0.6 ml of N,N-dimethylformamide, and the suspension was heated at reflux for 30 minutes. The reaction solution was concentrated under reduced pressure, 50 ml of benzene was added to the residue, and the mixture was stirred for 10 minutes. To the resulting suspension was added dropwise a mixture of 1.52 g (9.3 mmole) of 6-nitroxy-n-hexanol, 6.2 ml of triethylamine and 20 ml of benzene. After stirring for 4 hours, the reaction solution was poured into water, and extracted with ether (100 ml×2). The ethereal layer was successively with water and a saturated aqueous sodium chloride solution, dried over anhydrous sodium sulfate, and concentrated under reduced pressure to give 2 g of the crude product.

The crude product was purified by silica gel column chromatography [Wako-gel C-200 (trade name of Wako Junyaku Industries Co.), eluent: ether]. The eluted solution was concentrated, the residue was dissolved in 30 ml of ether, and hydrochloric acid gas was introduced into the solution. The precipitating hydrochloride was collected and recrystallized from methanol - ether to give 800 mg of the title compound as colorless prisms.

m.p. 145°–147° C.
$^1$H—NMR (DMSO—d$_6$, 200 MHz)δppm
11.75 (1H, s), 7.58 (1H, m),
7.1–7.3 (3H, m), 6.14 (1H, s),
5.05 (1H, s), 4.49 (2H, t, J=7 Hz),
4.35 (2H, t, J=7 Hz), 0.99 (3H, t, J=7 Hz).

In a similar manner, the following compounds were prepared.

3-Nitroxy-n-propyl apovincaminate hydrochloride m.p. 144°–145° C. (recrystallized from methanol-ether).
$^1$H—NMR (DMSO—d$_6$, 200 MHz)δppm
11.95 (1H, s), 7.58 (1H, m),
7.1–7.4 (3H, m), 6.20 (1H, s),
5.02 (1H, s), 4.65 (2H, t, J=7 Hz),
4.44 (2H, t, J=7 Hz), 0.99 (3H, t, J=7 Hz).
11-Nitroxy-n-undecyl apovincaminate hydrochloride m.p. 95°–98° C. (recrystallized from acetone - hexane)
$^1$H—NMR (DMSO—d$_6$, 200 MHz)δppm
11.9 (1H, br, s), 7.5–7.7 (1H, m),
7.1–7.3 (3H, m), 6.12 (1H, s),
5.04 (1H, br, s), 4.49 (2H, t, J=7 Hz),
4.35 (2H, t, J=7 Hz), 0.99 (3H, t, J=7 Hz).

EXAMPLE 3

Preparations of 2-nitroxyethyl apovincaminate

In 400 ml of N,N-dimethylformamide were suspended 66.4 g (0.20 mole) of apovincaminic acid, 40 g of (0.24 mole) of 2-nitroxyethyl bromide and 40 g (0.29 mole) of potassium carbonate, and the suspension was heated at 40° C. for 5 hours. The reaction solution was poured into 2 l of water, and extracted twice with 1 l of ethyl acetate. The organic layer was washed successively with water (1 l×2) and a saturated aqueous sodium chloride solution, dried over anhydrous sodium sulfate, and concentrated under reduced pressure. To the concentrate was added 500 ml of a mixture of ether and hexane (8:2) to give 64 g of the title compound as colorless needles.

m.p. 111°–112° C. (recrystallized from ether-n-hexane)
$^1$H—NMR (DMSO—d$_6$, 200 MHz)δppm 7.43 (1H, m), 7.23 (1H, m),
7.00–7.15 (2H, m), 6.19 (1H, s),
4.89 (2H, m), 4.66 (2H m), 4.08 (1H, s),
1.85 (2H, q, J=7 Hz), 0.95 (3H, t, J=7 Hz).

REFERENCE EXAMPLE 1

Preparation of 6-nitroxy-n-hexane-1-ol

In 300 ml of acetonitrile were dissolved 30 g of 6-bromo-n-hexane-1-ol and 42 g of silver nitrate, and the solution was stirred for 24 hours. The precipitating silver bromide was removed by filtration, and the acetonitrile solution was concentrated under reduced pressure. To the concentrate was added 200 ml of a saturated aqueous sodium solution, the precipitating silver chloride was removed by filtration, and the filtrate was extracted twice with 200 ml of ether. The extracts were dried over anhydrous sodium sulfate and concentrated to give 25 g of the title compound.

$^1$H—NMR (CDCl$_3$, 200 MHz)δppm
4.46 (2H, t, J=7 Hz), 3.65 (2H, t, J=7 Hz),
1.3–1.8 (8H, m)

In similar manner, the following compounds was prepared.

11-Nitroxy-n-undecane-1-ol
$^1$H—NMR (CDCLl$_3$, 200 MHz)δppm
4.45 (2H, t, J=7 hz), 3.63 (2H, t, J=7 Hz),
1.82 (2H, quintet, J=7 Hz),
1 57 (2H, quintet, J=7 Hz), 1.2–1.5 (14H, m).

EXPERIMENT 1

Effect on increase of blood flow

Effect on increase of blood flow was examined using dogs anesthetized with 5% pentbarbital sodium (30 mg/kg). The drugs [2-nitroxyethyl (+)-apovincaminate and 3-nitroxyl-n-propyl apovincaminate of the present invention and ethyl (+)-apovincaminate as control] were administered intraarterially in an amount of each 50 μg/kg, comparisons were made of the blood flows in the femoral artery, vertebral artery and common coronary artery before and after administration of the drugs, and the increase ratios of the blood flows were expressed by percent in Table 1.

TABLE 1

| Drug | Increase of blood flow (%) | | |
|---|---|---|---|
| | Femoral artery | Bertebral artery | Common coronary artery |
| Ethyl (+)—apovincaminate | 14.8 | 21.8 | 15.5 |
| 2-Nitroxyethyl (+)—apovincaminate | 86.8 | 72.3 | 71.1 |
| 3-Nitroxy-n-propyl (+)—apovincaminate | 28.2 | 45.7 | 44.3 |

EXPERIMENT 2

Inhibition of basilar and femoral artery construction

The test was carried out according to the method of Sonia Jancar et al described in European Journal of Pharmacology, vol. 136, page 345 (1987).

Mongrel dogs were killed by anesthetization with pentbarvital (60 mg/kg), the brain was rapidly removed, and the basilar artery was dissected. The femoral artery was picked up at the same time. The isolated blood vessel was cut into rings 5 mm wide, which were soaked in 5 ml of a Krebs-Ringer solution under a resting tension of 1 g. The solution was kept with 95% oxygen and 5% carbon dioxide.

To each of the solution in which the blood vessel rings were soaked were added 64 mM of potassium ion ($K^+$), $10^{-5}$ M of norepinefurin (NE) and $10^{-6}$ M of serotonine (5HT), respectively, and the resulting blood contractions were measured by FD pick up. To the blood vessel rings each was administered the drug [2-nitroxyethyl (+)-apovincaminate of the present invention and ethyl (+)-apovincaminate as control], and the concentrations ($IC_{50}$) required to produce 50% inhibitions of the contractions by the administration of $K^+$, NE and 5TH, respectively, were measured. The results were shown in Table 2.

TABLE 2

| Drug | $IC_{50}$ value (M) | | |
|---|---|---|---|
| | $K^+$ | NE | 5HT |
| A | $1.17 \times 10^{-6}$ | $2.23 \times 10^{-5}$ | $6.02 \times 10^{-6}$ |
| B | $2.50 \times 10^{-6}$ | $6.31 \times 10^{-5}$ | $1.00 \times 10^{-4}$ |

Note:
Drug A: 2-Nitroxyethyl (+)—apovincaminate
Drug B: Ethyl (+)—apovincaminate It is apparent from Table 2 that the compound of the present invention is as 2 times, 3 times and 10 times as strong as the control in terms of the inhibition of the $K^+$, NE and 5HT contractions, respectively.

EXPERIMENT 3

Improvement Of abnormalities of electroencephalogram (EEG) in aged rats

Six male Wistar rats (23–24 months old) were used for each group. The electrodes were implanted on the frontal and occipital cortexes and hippocamus, and the rats were housed for 14 days for applying to the test.

The rats operated were each put into an acoustically shielded box with the minimum light amount and tamed for 60 minutes while keeping the behavior free, and then the recording of EEG was started. Thirty minutes after the starting the recording of EEG, the drug (used the same as those in Experiment 2) dissolved in 1 ml of an aqueous vitamin C solution was intraperitoneally administered in the amount of 10 mg per 1 kg of the body weight of the rat. The spontaneous spindle bursts (abnormal EEG pattern in aged rats) were disappeared after the intraperitoneal administration and reappeared after a certain time. [Neurobiology of Aging, vol. 7, page 115 (1986)]. The time up to which the spontaneous spindle burst reappeared was measured. Group which received 10% aqueous vitamin C solution only was tested for comparison. The results were shown in Table 3.

TABLE 3

| Drug | Time up to which the spontaneous spindle burst reappeared (min) |
|---|---|
| Vitamin C | 10 |
| Drug A | 41 (31) |
| Drug B | 21 (11) |

Note:
Drug A: 2-Nitroxyethyl (+)—apovincaminate
Drug B: Ethyl (+)—apovincaminate Number in parentheses means the increment of the time (minutes) up to which the spontaneous spindle wave reappeared after the drug administration when compared with that of the group treated with vitamin C only.

It is apparent from Table 3 that the drug A (the compound of the present invention) is about 3 times as active as the drug B (control) in terms of the increment of the time up to which the spontaneous spindle burst reappeared after the drug administration.

What is claimed is:

1. An apovincaminic acid derivative represented by the formula

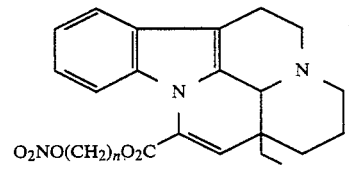

wherein n is an integer of from 2 to 11, and a pharmaceutically acceptable salt thereof.

2. 2-Nitroxyethyl apovincaminate.

3. 3-Nitroxy-n-propyl apovincaminate.